United States Patent [19]
Priest et al.

[11] Patent Number: 5,658,235
[45] Date of Patent: Aug. 19, 1997

[54] VIDEO OTOSCOPE AND OPTICAL LENS SYSTEM THEREFOR

[75] Inventors: Ronald A. Priest, Seminole, Fla.; Donald A. Carignan, Westfield, Mass.

[73] Assignee: MedRx, Inc., Seminole, Fla.

[21] Appl. No.: 414,351

[22] Filed: Mar. 31, 1995

[51] Int. Cl.$^6$ ................................................. A61B 1/227
[52] U.S. Cl. ............................................. 600/112; 600/200
[58] Field of Search ................................... 600/112, 200, 600/168, 176, 178; 359/362, 368, 369

[56] References Cited

U.S. PATENT DOCUMENTS

| | | | |
|---|---|---|---|
| 1,848,788 | 3/1932 | Loeck | 600/168 X |
| 1,952,759 | 3/1934 | König | 359/368 |
| 3,241,443 | 3/1966 | Rosenberger | 359/368 |
| 3,728,998 | 4/1973 | Heine | 600/200 |
| 4,335,713 | 6/1982 | Komiya | 600/114 |
| 4,593,973 | 6/1986 | Yoshida et al. | 385/126 |
| 4,643,171 | 2/1987 | Riester | 600/200 |
| 5,124,797 | 6/1992 | Williams et al. | 348/340 |
| 5,363,839 | 11/1994 | Lankford | 600/112 |
| 5,423,312 | 6/1995 | Siegmund et al. | 600/178 X |

*Primary Examiner*—Richard J. Apley
*Assistant Examiner*—David R. Risley
*Attorney, Agent, or Firm*—Neil F. Markva

[57] ABSTRACT

A video otoscope comprises an image forming assembly for producing an optical image of selected portions of an ear canal and a video camera for converting the optical image into a video image and transmitting the video image to a display system. The image forming assembly includes a speculum portion at a front end thereof, an optical lens system, and a coupling mechanism connecting the video camera to a rear end of the image forming assembly. The optical lens system is disposed along a longitudinal axis extending from a front distal end of the speculum portion to the video camera. The optical lens system includes an objective lens means disposed adjacent the front distal end and expander lens means spaced rearwardly from the objective lens along the longitudinal axis. Conically shaped inner taper tube surface defines a trapezoidal chamber portion around an optical image path that extends in a direction parallel to the longitudinal axis of an inner optical passage. The trapezoidal chamber portion is located between the objective lens and the expander lens. The objective lens has a first diameter and the expander lens has a second diameter greater than the first diameter of the objective lens. The speculum portion includes a light discharge aperture located around an outer periphery of the objective lens and a plurality of optic fiber elements that extend from a light source and into an annular light carrying chamber between an outer tube and an inner tube to direct light rays outwardly from the light source through the light discharge aperture.

33 Claims, 4 Drawing Sheets

VIDEO OTOSCOPE AND OPTICAL LENS SYSTEM THEREFOR

FIELD OF THE INVENTION

This invention relates to video otoscopes for examining the ear by producing optical images of selected portions of the outer ear canal. More particularly, the invention relates to an otoscope optical lens and speculum system providing enlarged optical images to be transmitted by video camera means to video display means.

BACKGROUND OF THE INVENTION

Otoscopes for examining the inner wall of the outer ear canal, tympanic membrane, and skeletal structures behind the membrane are well known. U.S. Pat. No. 5,239,984 discloses an otoscope having a beam splitter and coupling mechanism for attaching a video camera that transmits video images to display means such as a video monitor.

U.S. Pat. No. 5,363,839 discloses the present state of the art of the video otoscope having an elongated rod lens system in combination with a video camera having a focusing mechanism to provide the desired video image on various video display means. A relatively limited number of fiber optic elements disposed in a cylindrical annular light chamber around an elongated rod lens carry light to the distal end of the rod lens. An outer speculum member is removably mounted to the otoscope for retracting the ear canal opening when inserting the otoscope into the ear. The rod lens is subject to breakage and the overall otoscope structure is cumbersome to handle and operate.

The cylindrical rod lens of U.S. Pat. No. 5,363,839 includes several lens members disposed over an extended distance along the optical path. Consequently, the resultant otoscope length and structure impairs handling. The standard speculum is unsupported when placed over the projecting elongated cylindrical lens member.

U.S. Pat. Nos. 3,417,745; 4,281,910; 4,639,772; 4,651,202; 4,712,133; 4,870,950; 4,902,115; 4,979,498; 5,124,797; 5,188,094; and 5,235,965 each discloses a cylindrical type lens means for transmitting an optical image from a probe tip area to a means for displaying the optical image.

U.S. Pat. No. 4,858,002 shows a wide angle objective lens system for an endoscope that projects an optical image onto an image transducer. The overall length L between the distal end of the objective lens and the image transducer is less than twice the size of the diameter of the objective lens. This known wide angle objective lens system is used with the standard cylindrical rod lens but does not relate to the otoscope of this invention.

U.S. Pat. No. 4,766,886 discloses an otoscope device having an open rear portion for treating the inner ear canal or collecting substances from within the inner ear cavity. This device is for visual inspection of the ear canal and not for use with video camera display means.

U.S. Pat. Nos. 2,797,684; 3,812,847; 3,840,004; 3,949,740; and 4,380,998 show various types of speculum disposed on a solid tapered conical support structure. None of these support structures, however, operate in concert with a video camera means or light projecting means useful in obtaining video images by an optical scan of the ear canal.

The Purpose of the Invention

The primary object of the invention is to provide a reliable, durable, and simple structure of an otoscope lens and speculum system for use with available prior art speculum covers and that overcomes the various disadvantages associated with known video otoscopes.

Another object of the invention is to provide a tapered probe for an otoscope designed to provide a stable support surface for cerumen management tools.

Still another object is to provide an optical image forming assembly having a more manageable size and structure when connected to a video camera than other available video otoscopes.

Another object of the invention is to provide an image forming assembly for an otoscope and that includes an optical lens system that requires no focusing adjustment.

A still further object is to provide a fiber optic light source with a significantly increased light transmission efficiency compared to known otoscopes for producing an optical image displayed through video camera means.

Another object is to provide a video otoscope having a lens and speculum assembly having a structural integrity superior to otoscopes having elongated cylindrical lens structures.

SUMMARY OF THE INVENTION

The invention is directed to a video otoscope comprising optical image forming means for producing an optical image of selected portions of an ear canal and video camera means for converting the optical image into a video image for display. The image forming means includes a speculum portion at a front end of the image forming means, an optical lens system, and coupling means connecting the video camera means at a rear end of the image forming means.

The optical lens system is disposed along a longitudinal axis extending from a distal front end of the speculum portion to the video camera means. The lens system includes objective lens means disposed adjacent the front distal end of the speculum and expander lens means spaced rearwardly from the objective lens means along the longitudinal axis. Conically shaped inner taper tube means forms a trapezoidal chamber portion between the objective lens means and the expander lens means and around an optical image path that extends in a direction parallel to a longitudinal axis of an inner optical image passage. The objective lens means has a first diameter and the expander lens means has a second diameter greater than the first diameter of the objective lens means.

A specific embodiment of the image forming means includes a body portion having a front section connected to the speculum portion. The optical system directs an optical image along the optical image path from a reflective surface in the ear canal to a focal point of the objective lens means. The optical image is then enlarged by the expander lens means, which projects it through an inner passage of the body portion to video camera means.

More specifically, the focal point of the objective lens means forms an optical image within the inner taper tube means having an inner chamber surface that substantially precludes light reflection and glare within the trapezoidal chamber portion. The expander lens means picks up the optical image from the objective lens means, enlarges the optical image within the trapezoidal chamber, and relays an enlarged optical image through the body portion passage to the video camera means.

A particular feature of the objective lens means includes a front singlet lens member and a back singlet lens member disposed within a lens cell at the distal end of the speculum behind an end window. The expander lens means includes a front doublet lens member fixedly spaced from a back doublet lens member. An objective lens cell module includes a connecting end section attached to a front section of the body portion. The expander lens means is disposed in a front end cell of an expander lens cell module having a rear attaching section secured to a rear section of the body portion.

Another feature is directed to the speculum portion including a conically shaped outer taper tube having an inner tapered light chamber surface outwardly spaced from the inner taper tube means to form a conically shaped annular light carrying chamber between the inner taper tube means and the outer taper tube means. The outer taper tube means has an outer tapered surface for removably supporting a speculum cover member having a conically shaped surface for retracting the wall of the ear canal when a front distal end of the speculum portion is inserted into the ear canal.

The speculum portion includes light discharge means located around an outer periphery of the objective lens means. A plurality of optic fiber elements extend from a light source into the annular light carrying chamber to direct light rays outwardly through the light discharge means to a preselected portion of the reflective surface of the ear canal. In a specific embodiment, the light discharge means includes an outer end light transmitting cover or glass window located in front of the objective lens means.

Another feature of the invention comprises a nose cone member having a body portion connecting section and an outwardly projecting section with an outer surface shaped to support and attach the removably disposed specula cover member. A central opening in the projecting section is around the longitudinal axis of the optical image passage and around the optical image path along which the optical images pass rearwardly to the otoscope video camera.

The otoscope image forming assembly of the invention produces optical images of selected portions of an ear canal to be displayed as enlarged video images by video camera means. Display means electrically connected to the video camera means display the video image on either video monitor means, printer means, or video recorder means.

The otoscope image forming lens assembly of the invention produces clear optical images of selected portions of an ear canal without requiring a focus adjustment to display the optical images by video camera means. A wide angle objective lens means has a first diameter with a preselected depth of field and is located at a front end of the body portion to form an in-focus optical image along the longitudinal axis. Expander lens mounting means disposes expander lens means having a second diameter within the inner optical image passage at a location spaced rearwardly from the objective lens to enlarge the optical image along the optical image path. The second diameter of the expander lens means is greater than the first diameter of the objective lens means. Speculum means mounted to the front end of the body portion defines a trapezoidal chamber portion around the optical image path between the expander lens means and the objective lens means to allow enlargement of the optical image.

More specifically, the speculum means includes nose cone means having a nose cone member with a rear body portion connecting section and an outwardly projecting section with a central opening around the optical image path along which path the optical images pass rearwardly. The inner optical image passage includes a nose cone member receiving bore section that engages an outer surface of the rear body portion connecting section of the nose cone member.

Another feature of the invention comprises an objective lens cell module having objective lens means disposed in a cell at a front distal end section of the cell module, nose cone coupling means forming a rear distal end section having a front hub portion and a rear attaching portion. The front hub portion acts as an alignment means along the optical path.

Conically shaped inner taper tube means is disposed between the front and rear distal end sections of the objective lens cell module and has a structural configuration that forms the trapezoidal chamber portion. The nose cone member includes an objective lens cell module receiving section that fixedly engages an outer surface of the rear attaching portion of said nose cone coupling means. The front hub portion projects through the central opening of the nose cone member and the expander lens means is disposed rearwardly of the inner taper tube means.

Another feature of the conically shaped inner taper tube means is an inner tapered surface that is substantially non-reflective of light and forms the trapezoidal chamber portion. A conically shaped annular light carrying chamber is formed around the outside of the inner taper tube means by a laterally spaced shaped outer taper tube means.

The expander lens mounting means comprises an expander lens cell module having a rear body portion securing section and a front cell means for holding the expander lens means at a fixed location along the longitudinal axis. A rear body section of the image forming assembly includes means for receiving the rear body securing head section of the expander cell module. The rear body section includes means for coupling video camera means at a rear end of the inner optical image passage to receive an optical image projected along the optical image path through the objective lens means, the expander lens means, optical image filter means, and image diameter limiting means.

BRIEF DESCRIPTION OF THE DRAWINGS

Other objects of this invention will appear in the following description and appended claims, reference being made to the accompanying drawings forming a part of the specification wherein like reference characters designate corresponding parts in the several views.

DETAILED DESCRIPTION

The image forming assembly, generally designated 10, when coupled to video camera 40 comprises a video otoscope, generally designated 50, that meets all of the demands and requirements of a known optical otoscope and supports either a conventional disposable or reusable Welch-Allyn speculum 12 over a tapered metallic cone-shaped speculum projection or probe 14. That is, speculum 12 may be an ordinary disposable specula member or a reusable autoclavable speculum 3 mm or larger in diameter to be fitted over the conically shaped probe 14.

Projection 14 also houses coaxial fiber optic elements in light chamber 13 and includes inner tube 15 that defines a trapezoidal chamber portion of a unique optical system to be described below.

Probe 14 is connected to cone member 16 that is attached to front body section 21 of the optical image lens assembly, generally designated 20. Coupling mechanism 30 mounted to rear body section 24 comprises a standard C-mount used in the industry to connect video camera 40 to image forming assembly 10.

Figure 1:
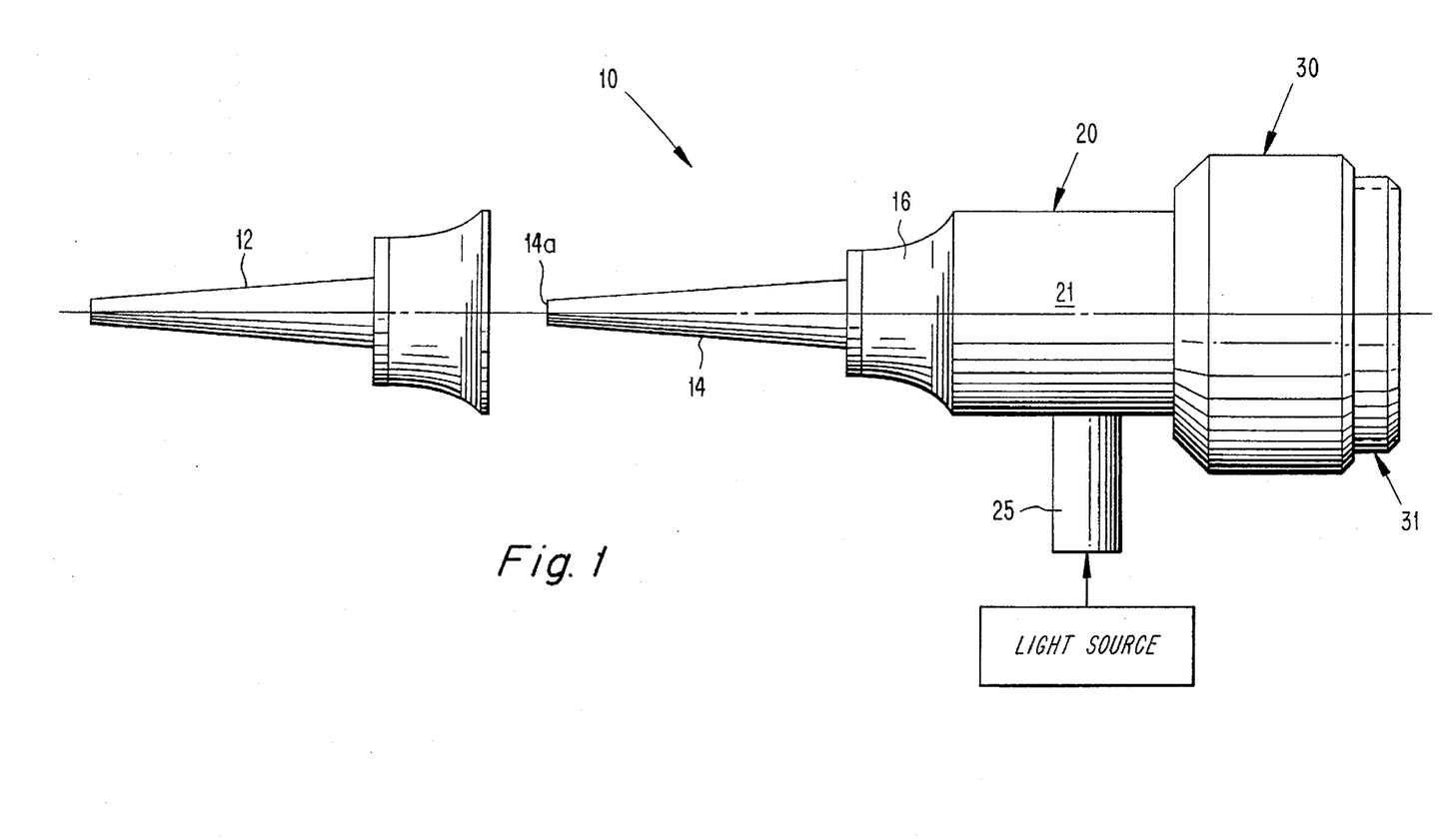
FIG. 1 is an exploded elevational view of an image forming assembly made in accordance with this invention.
Figure 2:
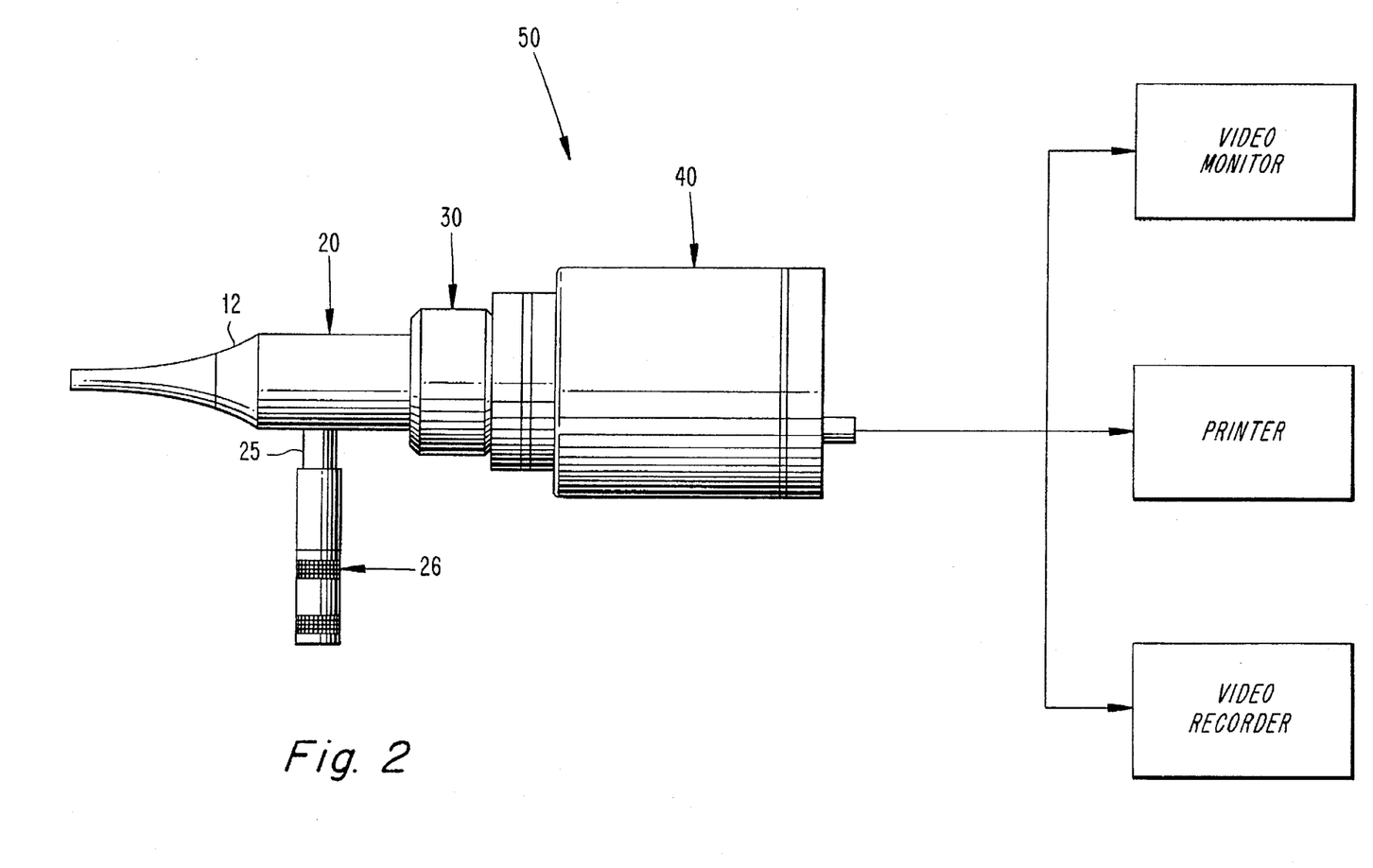
FIG. 2 is a side elevational view of a video otoscope of the invention.

The video otoscope 50 (FIG. 2) with its probe 14, optical image system, video camera 40, video monitor, video recorder and/or printer provide a video image of the tympanic membrane and surrounding ear canal in any available desired form when speculum 12, properly disposed on probe 14, is inserted into the ear canal.

The wide angle objective lens at the distal end 14a has a field of view of 62°. The depth of field is ⅜ of an inch ±⅛ of an inch from the outward tip 14a. When tip 14a is inserted into ear canal, it is located approximately ¼ inch away from the tympanic membrane. The location provides an optimum focal point for examination of the outer ear canal, the transition where the tympanic membrane is connected a distance beyond the translucent membrane for inspection of the middle ear bones and structure. With the wider angle of view made possible by the objective lens system in lens cell 11, a larger portion of the ear structure may be inspected as compared with other conventional optical otoscopes.

The field of view and depth of field provide an optical image having an in-focus perspective of the ear canal, the tympanic membrane, and shadows of the skeletal structure beyond the tympanic membrane. By obtaining such an in-focus optical image, video otoscope 50 does not require a focus ring for adjusting the focus to produce a clear image at the video camera.

The overall length from outer distal tip 14a to the rear of image forming assembly 10 is about 3¼ inches. With video camera 30 attached, the entire structure is about 5½ inches long.

In this embodiment, otoscope 50 (FIG. 2) includes a high resolution composite output 12 volt direct current color video camera 40 having a resolution of 420 lines. Video camera 40 in this specific embodiment is a readily available Watec 202. Camera 40 is electrically connectable in a known manner to either a video monitor, printer, or video recorder as shown.

In a specific embodiment, a Sony UP1200 color video printer having an on-board text character generator with a nonvolatile memory is electronically connected to camera 40. Printer information such as the name of the office, name of the attendant, the patient's name, and appropriate information up to 60 characters may be placed in the printer for identifying the high resolution print.

A foot switch (not shown) is connected in a known manner for safety reasons when using video otoscope 50. A foot switch can be configured to either create a hard copy print upon impression, freeze a picture for evaluation for possible printing at the operator's discretion. Such a printer is programmed using available software as desired.

The area around tip 14a is sealed and alcohol cleaned. Clear quartz glass element 14b is fixed to tip 14a with adhesive material. Kaylex urethane and Norland 81 are adhesive materials that may be used to bond the various body parts together. Tapered support probe 14 includes an outer stainless steel tapered tube 17 bonded to aluminum nose cone member 16. Body portion 20 comprises front body section 21 and rear body section 24 composed of aluminum may be soldered or otherwise adhered to aluminum nose cone member 16.

Stainless steel light post 25 carries fiber optic element bundle 25a connected to a light source by way of connector 26 of a fiber optic light cable. Thus, a plurality of fiber optic elements (not shown) directs light from the light source through fiber optic passageway 25b in nose cone 16, through light carrying chamber 13, and out an annular discharge aperture at tip 14a.

Figure 3:
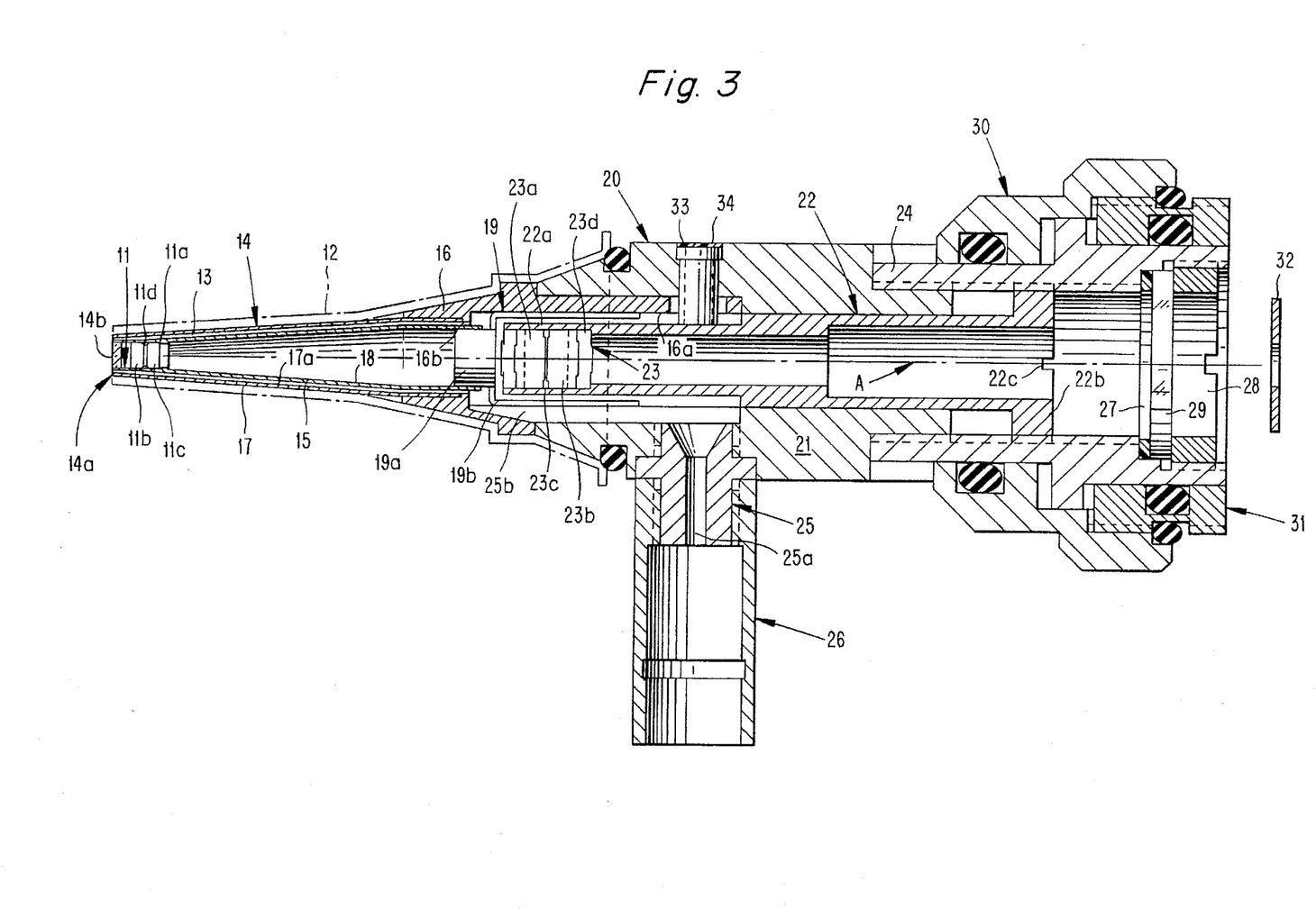
FIG. 3 is a diagrammatic longitudinal sectional view of an image forming assembly of the invention.
Figure 4:
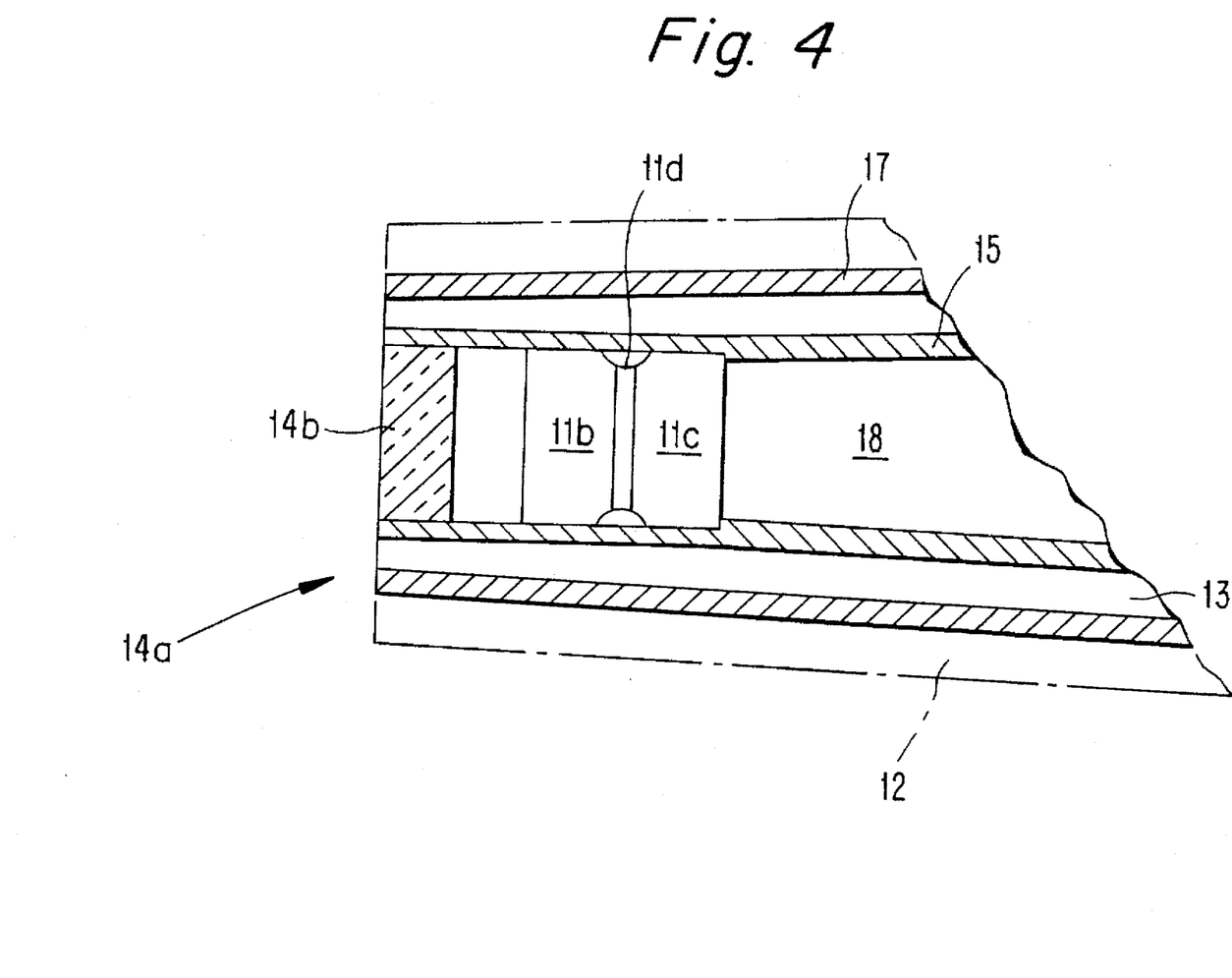
FIG. 4 is an enlarged detailed fragmentary sectional view of the objective lens cell structure of the invention.

Referring more specifically to FIG. 3, speculum 12 fits over cone shaped stainless steel probe 14 secured to nose cone 16 bonded to front body section 21. Outer distal tip end 14a includes an objective lens cell, generally designated 11, in inner taper tube member 15 having a shoulder 11a contiguously disposed to an objective lens assembly as shown. The objective lens assembly includes front singlet lens member 11b adhesively secured to back singlet lens 11c with spacer element 11d fixed therebetween forming an air space between lens members 11b and 11c. Lens member 11c fits against shoulder 11a and adhesive material bonds the objective lens system to the inside surface of lens cell 11.

Outer taper tube 17 has an inner chamber surface 17a laterally spaced from the outer surface of inner taper tube 15 to form a cone-shaped annular light chamber 13 between taper tube members 15 and 17. The outer surface of tube member 17 is adhesively secured to nose cone 16 as shown. The inside surface 18 of inner taper tube 15 is contiguously disposed to hub portion 19a of a nose cone coupling and aligning element, generally designated 19, for maintaining alignment of the optical image path within image forming assembly 20.

Element 19 has a front hub portion 19a and a rear attaching portion 19b bonded within receiving section 16a of cone member 16. Hub portion 19a projects into the inner end of tube 15 and through a central opening 16b of nose cone member 16. Rear connecting alignment member 19 slides in place after the fiber containing outer cone member 17 is bonded to the outwardly projecting portion of nose cone member 16 as shown.

Expander lens cell module 22 includes expander lens cell 22a in which expander lens assembly, generally designated 23, is disposed. Each doublet lens member 23a and 23b comprises two lenses bonded together in a known manner. In this specific embodiment, doublet lens members 23a and 23b are identical with the thinner lens element of each doublet facing outwardly from the lens combination as shown. Front doublet lens member 23a is secured at a laterally spaced distance from rear doublet lens member 23b with an annular spacer element 23c fixed therebetween forming an air space.

The doublet lens combination rests against seating member 23d contiguously placed against a shoulder in lens cell 22a of expander lens module 22 as shown. Adhesive material affixes the position of lens members 23a and 23b within lens cell 22a rearwardly of trapezoidal chamber portion of the optical image path that extends in a direction parallel to longitudinal axis A of the assembly.

The objective lens system including lens members 11b, 11c, and spacer 11d produces an optical image having a diameter of 1.6 mm. Expander lens assembly 23 picks up the optical image from the objective lens assembly, enlarges it to 3.6 mm, and relays the enlarged optical image to video camera 40 to be coupled at the outer end of image forming assembly 10. Thus, the optical image is magnified 2¼ times and relayed to the charge coupled device (CCD) of video camera 40 where it transforms the optical image to a video image for displaying on a desired display means. The video image is designed for a 3 inch format in the printer mode.

The optical image travels from a light reflective surface inside the ear canal through the objective lens system, and is enlarged by expander lens system 23 through the trapezoidal chamber portion of speculum projection 14. The trapezoidal chamber portion allows the optical image to expand from an initial diameter to a second magnified image diameter. Inner surface 18 of tube 15 defines the trapezoidal chamber portion and is substantially nonreflective of light to substantially eliminate light reflection and glare that would otherwise create darkening of the image. The anti-reflective or anti-glare inside surface 18 may be made by roughening the inside surface of the stainless steel through shot blasting or chemical etching.

Inner tapered light chamber surface 17a of tube 17 is spaced outwardly from inner taper tube 15 to form a conically shaped annular light carrying chamber 13 between inner tube 15 and outer tube 17. Thus, an annular light discharge aperture is located around the outer periphery of objective lens module 11.

A plurality of optic fiber elements extend from a light source into the annular light carrying chamber 13 to direct light rays outwardly from the annular shaped light discharge aperture as shown. Optic fiber cable 25a directs the plurality of optic fiber elements through fiber carrying channel 25b in nose cone 16 around hub portion 19a and into the annular light carrying chamber 13.

The amount of light coming from the light discharge aperture around objective lens cell 11 is a function of the number of fibers placed therearound. The CCD of the video camera is light sensitive. Thus, the more light provided to the inner ear canal to produce a reflected optical image is extremely important. With conically shaped annular light chamber 13, the efficiency of getting light into the ear canal for reflecting back to the light sensitive CCD of video camera 40 is maximized. With the amount of light delivered to the ear canal by the fiber optic elements, the optical system is optimized for producing the desired video image at a display means.

In constructing image forming assembly 10, before lens members 11b and 11c are placed in lens cell 11, the fiber optic elements are packed around the inner taper member 15 with the outer taper cone 17 placed over the fibers to protect and hold the fibers in place inside chamber 13. The tip of the fibers at the outer discharge aperture of light carrying chamber 13 is saturated with a fiber optic curing epoxy. Once the epoxy cures, the ends of the fibers are cut off. Tip 14a and fiber ends around the annular discharge aperture of light carrying chamber 13 are ground and polished.

Once the fiber optic placement process in probe 14 is complete, the objective lens combination is loaded into lens cell 11. Annular spacer ring 11d is placed into lens cell 11 after placement of rear lens member 11c. Lens members 11b and 11c are bonded to the ring member 11d and to the inside surface of cell 11. The fibers are then placed to extend through front body section 21 to fiber cable light post 25.

Hub portion 19a is disposed inside cone element 15 to effect alignment of the module along longitudinal axis A. The connecting section 19b is adhesively bonded to the inner surface 16a of nose cone body portion connecting section. Once the objective lens module is in place within front body section 21, expander lens cell module 22 is then inserted from the rear of image forming assembly 20 into rear body section 24.

Rear head section 22b of module 22 threadingly engages inside rear body section 24 that threadingly engages front body section 21 as shown. Screwdriving groove 22c in rear head section 22b is used to threadingly engage rear body section 24 and thereby move expander lens assembly 23 to produce an in-focus enlarged optical image to be impinged upon the charged couple device of video camera 40.

Three set screws 33 are located 120° from each other around the diameter of expander lens module 22 to effect alignment of lens cell module 22 for adjusting the optical image path with the inner optical image passage of body sections 21 and 24. Upon completion of the longitudinal alignment of expander lens module 22, an epoxy resin layer 34 is disposed and cured over each set screw 33 as shown. Thus, the possibility of misalignment occurring during use is obviated.

Once expander lens cell module 22 longitudinally locates and sets the focus of expander lens assembly 23 within body section 21, epoxy is used along the outer portion of rear head section 22b to fix module 22 in place.

After lens cell module 22 is fixed in place, silicone gasket 27 and color filter member 29 are secured using lock ring 28 threadingly engaging rear body section 24 as shown. Silicone gasket 27 is compression soft to allow glass filter member 29 to be held firmly in place by ring 28.

Delrin stop member 32 is annularly shaped to allow the enlarged optical image to pass therethrough while eliminating any fuzzy, out-of-focus edge portions of the enlarged optical image. Stop member 32 constitutes an iris or an aperture that provides a crisp round edge to the optical image that is projected onto the CCD of the video camera 40. The C-mount 31 of coupling member 30 is a standard coupling device enabling the rotation of image forming assembly 20 relative to camera 40. The O-rings as shown, provide the desired sealing function for attachment to video camera 40.

An important improvement in the assembly of this invention compared to known video otoscopes is in producing a clear, high resolution video image by minimizing the total number of lens members in the system. The glass in any lens member absorbs energy. Consequently, the more glass placed in the optical image path, the less is the efficiency of the optical system. With the optical system of this invention, the amount of glass is minimized and the shape of the enlarged image is maintained with clear resolution to the CCD.

While the VIDEO OTOSCOPE AND OPTICAL LENS SYSTEM THEREFOR has been shown and described in detail, it is obvious that this invention is not to be considered as limited to the exact form disclosed, and that changes in detail and construction may be made therein within the scope of the invention without departing from the spirit thereof.

Having thus set forth and disclosed the nature of this invention, what is claimed is:

1. A video otoscope comprising:
   a) image forming means for producing an optical image of selected portions of an ear canal; and
   b) video camera means for converting the optical image into a video image and transmitting said video image to display means;
   c) said image forming means including a conically shaped speculum portion having inner and outer tube means at a front end of the image forming means, an optical lens system, and coupling means connecting the video camera means at a rear end of the image forming means;
   d) said optical lens system being disposed along a longitudinal axis extending from a front distal end of the speculum portion to the video camera means;
   e) said optical lens system including objective lens means and expander lens means;
   f) said inner tube means including conically shaped inner taper tube means forming a trapezoidal chamber portion and having a distal end diameter and rear end diameter;

g) said trapezoidal chamber portion being disposed around an optical image path that extends in a direction parallel to the longitudinal axis between the objective lens means and the video camera means;

h) said objective lens means having a first diameter mounted to said distal end diameter of the inner taper tube means, and said expander lens means having a second diameter disposed adjacent said rear end diameter of the inner taper tube means, said second diameter being greater than said first diameter of the objective lens means.

2. An otoscope as defined in claim 1 wherein said image forming means includes a body portion having a front section connected to the speculum portion, said optical system directs an optical image which passes along the optical image path from a reflective surface in the ear canal and through the objective lens means to a focal point of the objective lens means, said optical image being enlarged by the expander lens means, and projected through a passage means in the body portion to said video camera means.

3. A video otoscope comprising:

a) image forming means for producing an optical image of selected portions of an ear canal; and b) video camera means for converting the optical image into a video image and transmitting said video image to display means;

c) said image forming means including a speculum portion at a front end of the image forming means, an optical lens system, and coupling means connecting the video camera means at a rear end of the image forming means;

d) said optical lens system being disposed along a longitudinal axis extending from a front distal end of the speculum portion to the video camera means;

e) said optical lens system including objective lens means disposed adjacent said front distal end, expander lens means spaced rearwardly from the objective lens means along said longitudinal axis, and conically shaped inner taper tube means forming a trapezoidal chamber portion around an optical image path that extends in a direction parallel to the longitudinal axis between the objective lens means and the video camera means;

f) said objective lens means having a first diameter and said expander lens means having a second diameter greater than said first diameter of the objective lens means;

g) said image forming means including a body portion having a front section connected to the speculum portion;

h) said optical system directs an optical image which passes along the optical image path from a reflective surface in the ear canal and through the objective lens means to a focal point of the objective lens means;

i) said optical image being enlarged by the expander lens means, and projected through a passage means in the body portion to said video camera means;

j) an inner taper tube means including an inner surface that substantially precludes light reflection within said trapezoidal chamber;

k) said focal point of the objective lens means locates an optical image within said inner surface of said inner taper tube means; and l) said expander lens means picks up said optical image along the optical image path, enlarges said optical image within the trapezoidal chamber, and relays an enlarged optical image through said passage means to said video camera means.

4. An otoscope as defined in claim 3 wherein said objective lens means includes a front singlet lens member and a back singlet lens member.

5. An otoscope as defined in claim 3 wherein said expander lens means includes a front doublet lens member and a back doublet lens member.

6. An otoscope as defined in claim 3 wherein said objective lens means is disposed in a front distal end cell of an objective lens module having a rear connecting end section attached to a front section of the body portion.

7. An otoscope as defined in claim 3 wherein said expander lens means is disposed in a front end cell of an expander lens cell module having a rear attaching section secured to a rear section of the body portion.

8. An otoscope as defined in claim 1 wherein the speculum portion includes a conically shaped outer taper tube means having an inner tapered surface outwardly spaced from the inner taper tube means to form a conically shaped annular light carrying chamber between the inner taper tube means and the outer taper tube means.

9. An otoscope as defined in claim 8 wherein the outer taper tube means has an outer tapered surface for removably supporting a specula cover member having a conically shaped surface means for retracting the wall of the ear canal when a front distal end of the speculum portion is inserted into the ear canal.

10. An otoscope as defined in claim 8 wherein the speculum portion includes light discharge means located around an outer periphery of the objective lens means and a plurality of optic fiber elements that extend from a light source and into the annular light carrying chamber to direct light rays outwardly from the light source through the light discharge means.

11. An otoscope as defined in claim 2 wherein the speculum portion includes a nose cone member having a body portion connecting section and an outwardly projecting section with an outer surface shaped to support a removably disposed specula cover member and with a central opening around the optical image path through which central opening the optical images pass rearwardly with respect to said otoscope into an inner passage of said body portion.

12. An otoscope image forming assembly for producing optical images of selected portions of an ear canal to be displayed as enlarged video images by video camera means, said image forming assembly comprising:

a) a tapered speculum portion at a front end of the assembly, an optical lens system, and video camera coupling means disposed at a rear end of the assembly;

b) said speculum portion including inner tube means having a conically shaped inner taper tube section with inner tapered surface means forming a trapezoidal chamber portion around an optical image path that extends in a direction parallel to a longitudinal axis between said front end of the assembly and the video camera coupling means;

c) said optical lens system including a first diameter objective lens means disposed within said inner tube means and adjacent mounted to said trapezoidal chamber portion at a distal portion of said front end of the assembly, and a second diameter expander lens means spaced rearwardly from the trapezoidal chamber portion with said second diameter being greater than said first diameter;

d) said optical lens system being effective to direct an optical image reflected from a selected portion of the ear canal along an optical image path through the objective lens means with the expander lens means enlarging and relaying the optical image through an inner passage of the assembly.

13. An image forming assembly as defined in claim 12 wherein said objective lens means forms an optical image to a focal point within said inner tapered surface means.

14. An image forming assembly as defined in claim 12 wherein the speculum portion includes conically shaped outer taper tube means having an inner tapered light chamber surface outwardly spaced from the inner taper tube section to form a conically shaped annular light carrying chamber between the inner taper tube section and the outer taper tube means.

15. An image forming assembly as defined in claim 14 wherein the outer taper tube means has an outer tapered surface for removably supporting a specula cover member having a conically shaped surface means for retracting the wall of the ear canal when a front distal end of the speculum portion is inserted into the ear canal.

16. An image forming assembly as defined in claim 14 wherein the speculum portion includes light discharge means located around an outer periphery of the objective lens means and a plurality of optic fiber elements that extend from a light source and into the annular light carrying chamber to direct light rays outwardly from the light source through the light discharge means.

17. An image forming assembly as defined in claim 13 wherein said objective lens means includes a front singlet lens member and a back singlet lens member, and the light discharge means includes an outer end light transmitting cover means located in front of the objective lens means.

18. An image forming assembly as defined in claim 14 wherein said expander lens means includes a front doublet lens member secured to a back doublet lens member at a laterally spaced distance with respect to each other.

19. An otoscope image forming assembly for producing optical images of selected portions of an ear canal to be displayed as enlarged video images by video camera means, said image forming assembly comprising:

a) a tapered speculum portion at a front end of the assembly, an optical lens system, and video camera coupling means disposed at a rear end of the assembly;

b) said speculum portion including inner taper tube means having conically shaped inner tapered surface means forming a trapezoidal chamber portion around an optical image path that extends in a direction parallel to a longitudinal axis between said front end of the assembly and the video camera coupling means;

c) said optical lens system including a first diameter objective lens means disposed adjacent said front end of the assembly, and a second diameter expander lens means spaced rearwardly from the trapezoidal chamber portion with said second diameter being greater than said first diameter;

d) said optical lens system being effective to direct an optical image reflected from a selected portion of the ear canal along an optical image path through the objective lens means with the expander lens means enlarging and relaying the optical image through an inner passage of the assembly;

e) said objective lens means is disposed in a front distal end cell of an objective lens cell module having a rear connecting end section attached to a front section of the body portion and forms an optical image to a focal point within said inner taper tube means.

20. An image forming assembly as defined in claim 19 wherein said expander lens means is disposed in a front end cell of an expander cell module having a rear attaching section secured to a rear section of the body portion.

21. An image forming assembly as defined in claim 12 wherein the speculum portion is mounted to a front end section of a body portion and includes a nose cone member having a body portion connecting section and an outwardly projecting section with an outer surface shaped to support a removably disposed specula cover member and with a central opening around said optical image path along which path the optical images pass rearwardly with respect to said otoscope into an inner passage of said body portion.

22. An otoscope image forming lens assembly for producing clear optical images of selected portions of an ear canal without requiring a focus adjustment to display said optical images by video camera means, said lens assembly comprising:

a) a body portion including an inner passage through the body portion and providing an optical image path that extends in a direction parallel to a longitudinal axis; and b) wide-angle objective lens means having a first diameter and a preselected depth of field, and being located at a front end of the body portion;

c) expander lens mounting means for disposing expander lens means having a second diameter within said inner passage at a location spaced rearwardly from the objective lens means to form an in-focus enlarged optical image along said optical image path;

d) said second diameter of the expander lens means being greater than said first diameter of the objective lens means;

e) conically shaped inner taper tube means mounted to the front end of the body portion to define a trapezoidal chamber portion around said optical image path between said expander lens means and said objective lens means to allow enlargement of said optical image, said objective lens means being mounted to a distal portion of said inner taper tube means; and f) nose cone means secured to the front end of the body portion and having a removably disposed specula cover member and an outer surface shaped to support said specula cover member around the trapezoidal chamber portion of said inner taper tube means;

g) said specula cover member having a conically shaped surface means for dilating the wall of the ear canal when a front distal end of the speculum cover member is inserted into the ear canal.

23. A lens assembly as defined in claim 22 wherein
said nose cone means includes a nose cone member having a body portion connecting section and an outwardly projecting section with a central opening around said optical image path along which path the optical images pass rearwardly into said inner passage.

24. A lens assembly as defined in claim 23 wherein
said inner passage includes a nose cone member receiving bore section which engages an outer surface of the rear body portion connecting section of the nose cone member.

25. An otoscope image forming lens assembly for producing clear optical images of selected portions of an ear canal without requiring a focus adjustment to display said optical images by video camera means, said lens assembly comprising:
   a) a body portion including an inner passage through the body portion and providing an optical image path that extends in a direction parallel to a longitudinal axis; and
   b) wide-angle objective lens means having a first diameter and a preselected depth of field, and being located at a front end of the body portion;
   c) expander lens mounting means for disposing expander lens means having a second diameter within said inner passage at a location spaced rearwardly from the objective lens means to form an in-focus enlarged optical image along said optical image path;
   d) said second diameter of the expander lens means being greater than said first diameter of the objective lens means; and
   e) speculum means mounted to the front end of the body portion to define a trapezoidal chamber portion around said optical image path between said expander lens means and said objective lens means to allow enlargement of said optical image;
   f) the speculum means including a front distal end and nose cone means secured to the front end of the body portion;
   g) said nose cone means including a removably disposed specula cover member and an outer surface shaped to support said specula cover member;
   h) said specula cover member having a conically shaped surface means for dilating the wall of the ear canal when the front distal end of the speculum means is inserted into the ear canal;
   i) said nose cone means including a nose cone member having a body portion connecting section and an outwardly projecting section with a central opening around said optical image path along which path the optical images pass rearwardly into said inner passage;
   j) the speculum means including an objective lens cell module having said objective lens means disposed in a cell at a front distal end section of the objective lens cell module, nose cone coupling means forming a rear distal end section having a front hub portion and a rear attaching portion, and conically shaped inner taper tube means disposed between said front and rear distal end sections of the objective lens cell module to form said trapezoidal chamber portion;
   k) the nose cone member including an objective lens cell module receiving section that fixedly engages an outer surface of the rear attaching portion of said nose cone coupling means.

26. A lens assembly as defined in claim 25 wherein
said front hub portion projects through said central opening of the nose cone member and said expander lens means is disposed rearwardly of the inner taper tube means.

27. An otoscope image forming lens assembly for producing clear optical images of selected portions of an ear canal without requiring a focus adjustment to display said optical images by video camera means, said lens assembly comprising:
   a) a body portion including an inner passage through the body portion and providing an optical image path that extends in a direction parallel to longitudinal axis; and
   b) wide-angel objective lens means having a first diameter and a preselected depth of field, and being located at a front end of the body portion;
   c) expander lens mounting means for disposing expander lens means having a second diameter within said inner passage at a location spaced rearwardly from the objective lens means to form an in-focus enlarged optical image along said optical image path;
   d) said second diameter of the expander lens means being greater than said first diameter of the objective lens means; and
   e) speculum means mounted to the front end of the body portion to define a trapezoidal chamber portion around said optical image path between said expander lens means and said objective lens means to allow enlargement of said optical image;
   f) the speculum means including conically shaped inner taper tube means having an inner tapered surface that is substantially nonreflective of light and forms said trapezoidal chamber portion and conically shaped outer taper tube means having an inner tapered light chamber surface outwardly spaced from the inner taper tube means to form a conically shaped annular light carrying chamber between the inner taper tube means and the outer taper tube means.

28. A lens assembly as defined in claim 27 wherein
the speculum means includes light discharge means located around an outer periphery of the objective lens means and a plurality of optic fiber elements extending from a light source and into the annular light carrying chamber to direct light rays outwardly from the speculum means through the light discharge means.

29. A lens assembly as defined in claim 28 wherein
said body portion includes a means for attaching fiber optic cable means having a plurality of optic fiber elements and means for directing the optic fiber elements from a light source to said annular light carrying chamber.

30. An otoscope image forming lens assembly for producing clear optical images of selected portions of an ear canal without requiring a focus adjustment to display said optical images by video camera means, said lens assembly comprising:
   a) a body portion including an inner passage through the body portion and providing an optical image path that extends in a direction parallel to a longitudinal axis; and
   b) wide-angle objective lens means having a first diameter and a preselected depth of field, and being located at a front end of the body portion;
   c) expander lens mounting means for disposing expander lens means having a second diameter within said inner passage at a location spaced rearwardly from the objective lens means to form an in-focus enlarged optical image along said optical image path;

d) said second diameter of the expander lens means being greater than said first diameter of the objective lens means; and e) speculum means mounted to the front end of the body portion to define a trapezoidal chamber portion around said optical image path between said expander lens means and said objective lens means to allow enlargement of said optical image;

f) said expander lens mounting means including an expander lens cell module having a rear body passage securing section and a front cell means for holding the expander lens means at a fixed location along said longitudinal axis;

g) said inner passage including rear bore section means for receiving said rear body passage securing section of the expander cell module at a rear end section of the body portion.

31. A lens assembly as defined in claim 30 wherein said body portion includes means for coupling video camera means at a rear end of said inner passage to receive an optical image projected along said optical image path that extends through said objective lens means, said expander lens means, optical image filter means, and image diameter limiting means.

32. An otoscope as defined in claim 1 wherein said display means includes means electrically connected to said video camera means for displaying said video image.

33. An otoscope as defined in claim 32 wherein said display means includes video monitor means, printer means, and video recorder means.

* * * * *